US006723537B2

(12) United States Patent
Peelle

(10) Patent No.: US 6,723,537 B2
(45) Date of Patent: Apr. 20, 2004

(54) DIRECTED EVOLUTION OF PROTEIN IN MAMMALIAN CELLS

(75) Inventor: Beau Peelle, Somerville, MA (US)

(73) Assignees: Rigel Pharmaceuticals, Incorporated, South San Francisco, CA (US); Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/152,296

(22) Filed: May 20, 2002

(65) Prior Publication Data

US 2003/0077730 A1 Apr. 24, 2003

Related U.S. Application Data

(60) Provisional application No. 60/291,871, filed on May 18, 2001.

(51) Int. Cl.[7] .................................................. C12P 21/06

(52) U.S. Cl. ......................... 435/69.1; 435/69.1; 435/6; 536/23.1; 530/350

(58) Field of Search ............................ 536/23.1; 435/6, 435/69.1; 530/350

(56) References Cited

U.S. PATENT DOCUMENTS 5,811,238 A 9/1998 Stemmer et al. ............... 435/6

FOREIGN PATENT DOCUMENTS

| | | |
|---|---|---|
| WO | WO 95/21191 A1 | 8/1995 |
| WO | WO 99/41368 A2 | 8/1999 |
| WO | WO 99/41369 A2 | 8/1999 |
| WO | WO 99/45143 A2 | 9/1999 |
| WO | WO 00/22115 A2 | 4/2000 |
| WO | WO 00/64344 A2 | 8/2000 |
| WO | WO 00/73433 | 12/2000 |
| WO | WO 01/04287 | 1/2001 |

OTHER PUBLICATIONS

Matsumura et al., *Protein Science* 8: 731–740 (1990).
Leung et al., *Technique–A Journal of Methods in Cell and Molecular Biology* 1:1: 11–15 (1989).
Gross et al., *PNAS* 97:22 11990–11995 (2000).
Gram et al., *Proc. Natl. Acad. Sci.*:89: 3576–3580 (1992).
Cadwell et al., *PCR Methods and Applications* 2: 28–33 (1992).
Baird et al., *PNAS* 97:22: 11984–11989 (2000).
Prasher, *TIG* 11:8: 320–323 (1995).
Prasher et al., *Gene*. 111: 229–233 (1992).
Heim et al., *Proc. Natl. Acad. Sci.* 91: 12501–12504 (1994).
Tsien, *Annu. Rev. Biochem.* 67: 509–544 (1998).
Yarbrough et al., *PNAS* 98:2: 462–467 (2001).
Wall et al., *Nature Structural Biology* 7:12: 1133–1138 (2000).
Chalfie et al., *Science* 263: 802–805 (1994).
Heim et al., *Nature* 373: 663–664 (1995).
Tsien, *Nature Biotechnology* 17: 956–957 (1999).
Matz et al., *Nature Biotechnology* 17: 969–973 (1999).
Wiehler et al., FEBS Letters, vol. 487, pp. 384–389, 2001.*
Database AGeneSeq (GPX BIOTECH AG), Accession No. ABB08835, "New DNA encoding Red Fluorescent Protein, useful as Marker in Biotechnology has sequence optimized for expression in eukaryotes, especially yeast or plants", DE 20001395, Abstract, Mar. 2001.

* cited by examiner

*Primary Examiner*—Karen Cochrane Carlson
*Assistant Examiner*—Hope A. Robinson
(74) *Attorney, Agent, or Firm*—Townsend and Townsend and Crew LLP

(57) ABSTRACT

The present invention relates to directed protein evolution in mammalian cells and improved mutants of Discosoma sp. red fluorescent proteins.

31 Claims, 7 Drawing Sheets

DNA and translated protein sequence of codon optimized wt DsRED protein

```
1/1                                     31/11
ATG GTG CGC TCC TCC AAG AAC GTC ATC AAG GAG TTC ATG CGC TTC AAG GTG CGC ATG GAG
M   V   R   S   S   K   N   V   I   K   E   F   M   R   F   K   V   R   M   E
61/21                                   91/31
GGC ACC GTG AAC GGC CAC GAG TTC GAG ATC GAG GGC GAG GGC GAG GGC CGC CCC TAC GAG
G   T   V   N   G   H   E   F   E   I   E   G   E   G   E   G   R   P   Y   E
121/41                                  151/51
GGC CAC AAC ACC GTG AAG CTG AAG GTG ACC AAG GGC GGC CCC CTG CCC TTC GCC TGG GAC
G   H   N   T   V   K   L   K   V   T   K   G   G   P   L   P   F   A   W   D
181/61                                  211/71
ATC CTG TCC CCC CAG TTC CAG TAC GGC TCC AAG GTG TAC GTG AAG CAC CCC GCC GAC ATC
I   L   S   P   Q   F   Q   Y   G   S   K   V   Y   V   K   H   P   A   D   I
241/81                                  271/91
CCC GAC TAC AAG AAG CTG TCC TTC CCC GAG GGC TTC AAG TGG GAG CGC GTG ATG AAC TTC
P   D   Y   K   K   L   S   F   P   E   G   F   K   W   E   R   V   M   N   F
301/101                                 331/111
GAG GAC GGC GGC GTG GTG ACC GTG ACC CAG GAC TCC TCC CTG CAG GAC GGC TGC TTC ATC
E   D   G   G   V   V   T   V   T   Q   D   S   S   L   Q   D   G   C   F   I
361/121                                 391/131
TAC AAG GTG AAG TTC ATC GGC GTG AAC TTC CCC TCC GAC GGC CCC GTA ATG CAG AAG AAG
Y   K   V   K   F   I   G   V   N   F   P   S   D   G   P   V   M   Q   K   K
421/141                                 451/151
ACC ATG GGC TGG GAG GCC TCC ACC GAG CGC CTG TAC CCC CGC GAC GGC GTG CTG AAG GGC
T   M   G   W   E   A   S   T   E   R   L   Y   P   R   D   G   V   L   K   G
```

FIG. 1.

```
481/161                                         511/171
GAG ATC CAC AAG GCC CTG AAG CTG AAG GAC GGC GGC CAC TAC CTG GTG GAG TTC AAG agt
E   I   H   K   A   L   K   L   K   D   G   G   H   Y   L   V   E   F   K   S
541/181                                         571/191
ATC TAC ATG GCC AAG AAG CCC GTG CAG CTG CCC GGC TAC TAC TAC GTG GAC TCC AAG CTG
I   Y   M   A   K   K   P   V   Q   L   P   G   Y   Y   Y   V   D   S   K   L
601/201                                         631/211
GAC ATC ACC TCC CAC AAC GAG GAC TAC ACC ATC GTG GAG CAG TAC GAG CGC ACC GAG GGC
D   I   T   S   H   N   E   D   Y   T   I   V   E   Q   Y   E   R   T   E   G
661/221                                         691/231
CGC CAC CAC CTG TTC CTG gag gag gcc gcc aag gcc gac tac aag gac gac gac gac aag
R   H   H   L   F   L   E   E   A   A   K   A   D   Y   K   D   D   D   D   K
721/241
TAG
*
```

List of confirmed Mutations from screen:
N24S, N24R, N24H (boxed)
F125L, and F125V (boxed)
K164M (boxed)
M183K (boxed)

*FIG. 1.* (CONTINUED)

Brightest clones by mean FL2 fluorescence

| Clone | $m_{G(FL2)}$ | %FL2+ | $m_G$ retest | %FL2+ | mutations | identical/48 |
|---|---|---|---|---|---|---|
| 1-A12 | 229 | 16 | 101 | 4.2 | F124L,M182K+ | 1 |
| 2-A04 | 189 | 27.4 | 98 | 3.1 | F124L,M182K,K138 | 0 |
| 1-G09 | 186 | 17.8 | 97 | 4.7 | F124L,M182K,N23S+ | 2 |
| 1-A09 | 204 | 19.7 | 85 | 4.5 | F124L,M182K,N23S,R18H | 1(-182K) |
| 2-D02 | 179 | 30.1 | 82 | 3 | F124V,M182 | 1 |
| 1-H02 | 145 | 18.6 | 81 | 4.5 | K163M | 1 |
| 1-E04 | 130 | 21.6 | 78 | 3.3 | K163M | 0 |
| 1-G12 | 118 | 16.7 | 61 | 4.8 | F124L,E149D,D170G | 0 |
| 2-G01 | 122 | 21 | 44 | 3.6 | F124L | 13 |
| AsFED | | - | 17 | 1.7 | wt | - |
| dsREDcflag | - | - | <2 | 0 | wt | - |

by mutation: 46 F124L/V, 8 F124 + M182
(out of 48) 10 M182K/T 5 N23 + F124
8 N23S/R/H, 3 K92R

FIG. 3.

SEQUENCE LISTING

<160> NUMBER OF SEQ ID NOS: 2

<210> SEQ ID NO 1<br>
<211> LENGTH: 723<br>
<212> TYPE: DNA<br>
<213> ORGANISM: Artificial Sequence<br>
<220> FEATURE:<br>
<223> OTHER INFORMATION: Description of Artificial Sequence:mammalian codon-optimized variant (DsRED) of Discosoma sp. "red" red fluorescent protein (RFP)<br>
<220> FEATURE:<br>
<221> NAME/KEY: CDS<br>
<222> LOCATION: (1)..(723)<br>
<223> OTHER INFORMATION: DsRED

<400> SEQUENCE: 1

```
atg gtg cgc tcc tcc aag aac gtc atc aag gag ttc atg cgc ttc aag       48
Met Val Arg Ser Ser Lys Asn Val Ile Lys Glu Phe Met Arg Phe Lys
  1               5                  10                  15

gtg cgc atg gag ggc acc gtg aac ggc cac gag ttc gag atc gag ggc       96
```

-continued

```
Val Arg Met Glu Gly Thr Val Asn Gly His Glu Phe Glu Ile Glu Gly
             20                  25                  30

gag ggc gag ggc cgc ccc tac gag ggc cac aac acc gtg aag ctg aag      144
Glu Gly Glu Gly Arg Pro Tyr Glu Gly His Asn Thr Val Lys Leu Lys
        35                  40                  45

gtg acc aag ggc ggc ccc ctg ccc ttc gcc tgg gac atc ctg tcc ccc      192
Val Thr Lys Gly Gly Pro Leu Pro Phe Ala Trp Asp Ile Leu Ser Pro
    50                  55                  60

cag ttc cag tac ggc tcc aag gtg tac gtg aag cac ccc gcc gac atc      240
Gln Phe Gln Tyr Gly Ser Lys Val Tyr Val Lys His Pro Ala Asp Ile
 65                  70                  75                  80

ccc gac tac aag aag ctg tcc ttc ccc gag ggc ttc aag tgg gag cgc      288
Pro Asp Tyr Lys Lys Leu Ser Phe Pro Glu Gly Phe Lys Trp Glu Arg
                 85                  90                  95

gtg atg aac ttc gag gac ggc ggc gtg gtg acc gtg acc cag gac tcc      336
Val Met Asn Phe Glu Asp Gly Gly Val Val Thr Val Thr Gln Asp Ser
            100                 105                 110

tcc ctg cag gac ggc tgc ttc atc tac aag gtg aag ttc atc ggc gtg      384
Ser Leu Gln Asp Gly Cys Phe Ile Tyr Lys Val Lys Phe Ile Gly Val
        115                 120                 125

aac ttc ccc tcc gac ggc ccc gta atg cag aag aag acc atg ggc tgg      432
Asn Phe Pro Ser Asp Gly Pro Val Met Gln Lys Lys Thr Met Gly Trp
    130                 135                 140

gag gcc tcc acc gag cgc ctg tac ccc cgc gac ggc gtg ctg aag ggc      480
Glu Ala Ser Thr Glu Arg Leu Tyr Pro Arg Asp Gly Val Leu Lys Gly
145                 150                 155                 160

gag atc cac aag gcc ctg aag ctg aag gac ggc ggc cac tac ctg gtg      528
Glu Ile His Lys Ala Leu Lys Leu Lys Asp Gly Gly His Tyr Leu Val
                165                 170                 175

gag ttc aag agt atc tac atg gcc aag aag ccc gtg cag ctg ccc ggc      576
Glu Phe Lys Ser Ile Tyr Met Ala Lys Lys Pro Val Gln Leu Pro Gly
            180                 185                 190

tac tac tac gtg gac tcc aag ctg gac atc acc tcc cac aac gag gac      624
Tyr Tyr Tyr Val Asp Ser Lys Leu Asp Ile Thr Ser His Asn Glu Asp
        195                 200                 205

tac acc atc gtg gag cag tac gag cgc acc gag ggc cgc cac cac ctg      672
Tyr Thr Ile Val Glu Gln Tyr Glu Arg Thr Glu Gly Arg His His Leu
    210                 215                 220

ttc ctg gag gag gcc gcc aag gcc gac tac aag gac gac gac gac aag      720
Phe Leu Glu Glu Ala Ala Lys Ala Asp Tyr Lys Asp Asp Asp Asp Lys
225                 230                 235                 240

tag                                                                  723


<210> SEQ ID NO 2
<211> LENGTH: 240
<212> TYPE: PRT
<213> ORGANISM: Artificial Sequence
<220> FEATURE:
<223> OTHER INFORMATION: Description of Artificial Sequence:mammalian
      codon-optimized variant (DsRED) of Discosoma sp.
      "red" red fluorescent protein (RFP)

<400> SEQUENCE: 2

Met Val Arg Ser Ser Lys Asn Val Ile Lys Glu Phe Met Arg Phe Lys
  1               5                  10                  15

Val Arg Met Glu Gly Thr Val Asn Gly His Glu Phe Glu Ile Glu Gly
             20                  25                  30

Glu Gly Glu Gly Arg Pro Tyr Glu Gly His Asn Thr Val Lys Leu Lys
        35                  40                  45

Val Thr Lys Gly Gly Pro Leu Pro Phe Ala Trp Asp Ile Leu Ser Pro
```

-continued

```
        50                  55                  60

Gln Phe Gln Tyr Gly Ser Lys Val Tyr Val Lys His Pro Ala Asp Ile
 65                 70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Cys Phe Ile Tyr Lys Val Lys Phe Ile Gly Val
        115                 120                 125

Asn Phe Pro Ser Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Lys Ala Leu Lys Leu Lys Asp Gly Gly His Tyr Leu Val
                165                 170                 175

Glu Phe Lys Ser Ile Tyr Met Ala Lys Lys Pro Val Gln Leu Pro Gly
            180                 185                 190

Tyr Tyr Tyr Val Asp Ser Lys Leu Asp Ile Thr Ser His Asn Glu Asp
        195                 200                 205

Tyr Thr Ile Val Glu Gln Tyr Glu Arg Thr Glu Gly Arg His His Leu
    210                 215                 220

Phe Leu Glu Glu Ala Ala Lys Ala Asp Tyr Lys Asp Asp Asp Asp Lys
225                 230                 235                 240
```

DIRECTED EVOLUTION OF PROTEIN IN MAMMALIAN CELLS

CROSS-REFERENCES TO RELATED APPLICATIONS

The present application claims priority to U.S. Ser. No. 60/291,871, filed May 18, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

1. Field of the Invention

The present invention relates to directed protein evolution in mammalian cells and improved mutants of Discosoma sp. red fluorescent proteins.

2. Background of the Invention

Red fluorescent protein has been isolated from a Discosoma sp. and sequenced (see, e.g., Matz et al., Nature Biotech. 17:969–973 (1999), Gross et al., *Proc. Nat'l Acad. Sci. USA* 97:11990–11995 (2000)). A variant with humanized codons has also been engineered (Clontech, "DSREDT™"). The crystal structure of red fluorescent protein has been elucidated, which demonstrated that red fluorescent protein is a tetrameric protein (Wall et al., *Nat. Struc. Biol.* 7:1089 (2000); Yarbrough et al., *Proc. Nat'l Acad. Sci USA* 16:462–467 (2000)).

Red fluorescent protein (RFP) and DsRED, as well as other fluorescent proteins such as YFP, or GFP from *Aequorea Victoria, Renilla reniformis, Renilla muelleri,* and *Ptilosarcus gurneyi,* are useful are reporter molecules for a variety of bioassays, including those that use FACS as a selection mechanism (see, e.g., Tsein, *Nature Biotechnology* 17:956 (1999); Tsein, *Ann. Rev. Biochem.* 6:509–544 (1998); Heim et al., *Nature* 373:663–664 (1995); Heim et al., *Proc. Nat'l Acad. Sci. USA* 91:1250 (1994); Prasher et al., *Gene* 111:229 (1992); Prasher et al., *Trends in Genetics* 11:320 (1995); Chalfie et al., *Science* 263:802 (1994); and WO 95/21191). However, brighter, faster folding, and higher expressing variants would be useful.

Such variants can be made, e.g., using methods of gene shuffling and mutagenesis (see, e.g., U.S. Pat. No. 5,811,238; WO 00/73433; WO 00/22115; WO 99/41369; WO 01/04287; WO 00/46344; WO 99/45143, WO 99/41368; and Ichiro et al., *Protein Science* 8:731–740 (1999)). However, the use of such methods for production of variant proteins such as Discosoma red fluorescent protein variants is not always successful (see, e.g., Baird et al., *Proc. Nat'l Acad. Sci. USA* 97:11984–11989 (2000)). Novel methods of making such variants would therefore be useful.

SUMMARY OF THE INVENTION

The present invention therefore provides variants of Discosoma red fluorescent protein that have been generated using directed molecular evolution in mammalian cells. The variants of the invention have greatly improved brightness, expression, and/or folding kinetics as compared to wild type or a codon optimized variant. The present invention also provides novel methods of directed protein evolution in mammalian cells using retroviral gene transfer and FACS sorting. Such methods can be used to provide improved variants of fluorescent proteins such as Discosoma red fluorescent protein and fluorescent proteins from other sources, such as *Aequorea victoria, Renilla reniformis, Renilla muelleri,* and *Ptilosarcus gurneyi.*

In one aspect, the present invention provides an isolated Discosoma red fluorescent protein, the protein comprising an amino acid sequence as shown in FIG. 1 with one or more point mutations at an amino acid position selected from the group consisting of N24, F125, K164, and M183.

In one embodiment, the protein comprises two, three, or four point mutations at an amino acid position selected from the group consisting of N24, F125, K164, and M183.

In one embodiment, the point mutation at amino acid position N24 is a serine, arginine, or histidine substitution. In another embodiment, the point mutation at amino acid position F125 is a leucine or valine substitution. In another embodiment, the point mutation at amino acid position K164 is a methionine substitution. In another embodiment, the point mutation at amino acid position M183 is a lysine or threonine substitution.

In one embodiment, the protein comprises an amino acid sequence as shown in FIG. 1 with a leucine or valine substitution at amino acid position F125 and a lysine substitution at amino acid position M183. In another embodiment, the protein comprises an amino acid sequence as shown in FIG. 1 with a leucine substitution at amino acid position F125 and a lysine substitution at amino acid position M183. In another embodiment, the protein comprises an amino acid sequence as shown in FIG. 1 with a valine substitution at amino acid position F125 and a lysine substitution at amino acid position M183.

In one embodiment, the protein comprises an amino acid sequence as shown in FIG. 1 with a leucine or valine substitution at amino acid position F125 and a serine, arginine, or histidine substitution at amino acid position N24. In another embodiment, the protein comprises an amino acid sequence as shown in FIG. 1 with a leucine substitution at amino acid position F125 and a serine substitution at amino acid position N24.

In one embodiment, the protein comprises an amino acid sequence as shown in FIG. 1 with a leucine or valine substitution at amino acid position F125, a serine, arginine, or histidine substitution at amino acid position N24, and a lysine substitution at amino acid position M183. In another embodiment, the protein comprises an amino acid sequence as shown in FIG. 1 with a leucine substitution at amino acid position F125, a serine substitution at amino acid position N24, and a lysine substitution at amino acid position M183.

In one embodiment, the protein comprises an amino acid sequence as shown in FIG. 1 with a methionine substitution at amino acid position K164.

In one embodiment, the protein comprises an amino acid sequence as shown in FIG. 1 with a leucine substitution at amino acid position F125.

In one embodiment, the protein further comprises one or more point mutations at an amino acid position selected from the group consisting of K93, R18, K139, E149, and D170. In another embodiment, the point mutation at amino acid position K93 is an arginine substitution. In another embodiment, the point mutation at amino acid position R18 is a histidine substitution. In another embodiment, the point mutation at amino acid position E149 is an aspartic acid substitution. In another embodiment, the point mutation at amino acid position D170 is a glycine substitution.

In one embodiment, the protein comprises an amino acid sequence as shown in FIG. 1 with a leucine substitution at amino acid position F125, a serine substitution at amino acid position N24, a lysine substitution at amino acid position M183, and a histidine substitution at amino acid position R18.

In one embodiment, the protein comprises an amino acid sequence as shown in FIG. 1 with a leucine substitution at amino acid position F125, a aspartic acid substitution at amino acid position E149, and a glycine substitution at amino acid position D170.

In one aspect, the present invention provides a Discosoma red fluorescent protein that is a fusion protein.

In another aspect, the present invention provides a nucleic acid encoding the Discosoma red fluorescent protein of the invention. In one embodiment, the nucleic acid is codon-optimized for mammalian expression. In another embodiment, the nucleic acid encodes a fusion protein.

In another aspect, the present invention provides a vector comprising a nucleic acid encoding the Discosoma red fluorescent protein of the invention. In one embodiment, the vector is a retroviral vector.

In another aspect, the present invention provides a host cell comprising the vector of the invention.

In another aspect, the present invention provides a retroviral cDNA expression library comprising a nucleic acid encoding the Discosoma red fluorescent protein.

In another aspect, the present invention provides a method of making a protein variant, the method comprising the steps of: (i) mutating a selected nucleotide sequence encoding a fluorescent protein; (ii) cloning the mutated sequences into an expression vector; (iii) transfecting mammalian cells with the expression vector; and (iv) identifying the variants.

In one embodiment, the protein is a fluorescent protein and variants are identified by FACS analysis. In another embodiment, the selected nucleotide sequence encodes a fluorescent protein from Discosoma "red" sp., *Aequorea Victoria, Renilla reniformis, Renilla muelleri,* or *Ptilosarcus gurneyi.*

In one embodiment, the selected nucleotide sequence is mutated using error prone PCR.

In another embodiment, the expression vector is a retroviral expression vector.

In another aspect, the present invention provides a method of making a fluorescent protein variant, the method comprising the steps of: (i) mutating by error prone PCR a selected nucleotide sequence encoding a fluorescent protein; (ii) cloning the mutated sequences into a retroviral expression vector; (iii) transfecting mammalian cells with the expression vector; and (iv) selecting variants using FACS analysis.

In one embodiment, the selected nucleotide sequence encodes a fluorescent protein from Discosoma "red" sp., *Aequorea Victoria, Renilla reniformis, Renilla muelleri,* or *Ptilosarcus gurneyi.*

BRIEF DESCRIPTION OF THE DRAWINGS

FIG. 1 provides the amino acid (SEQ ID NO:2) and nucleotide (SEQ ID NO:1) sequence of a mammalian codon optimized Discosoma red fluorescent protein. This figure also indicates preferred point mutations in the amino acid sequence for variants.

FIG. 3 provides a list of mutated Discosoma red fluorescent proteins isolated using the mammalian directed evolution methods of the invention.

DETAILED DESCRIPTION OF THE INVENTION

Figure 2:
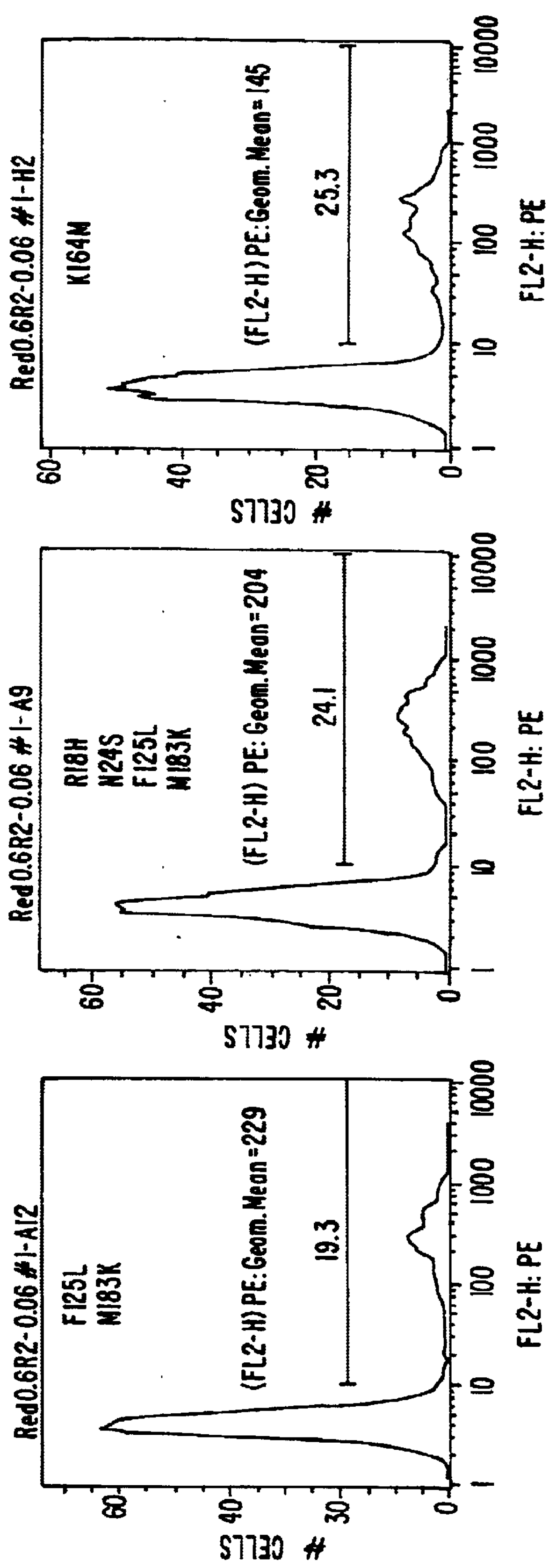
FIG. 2 provides examples of brighter Discosoma red fluorescent protein variants.
Figure 2:
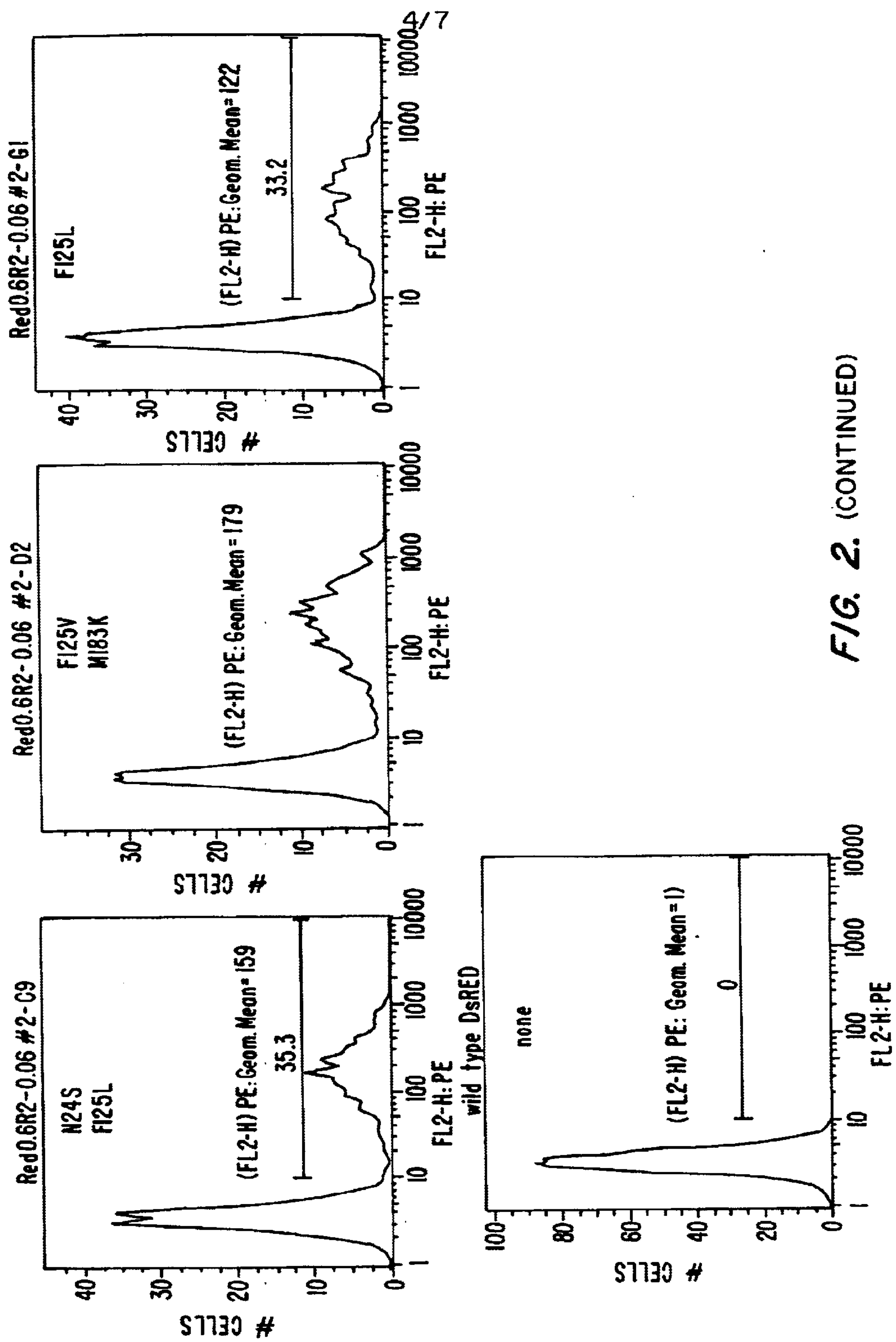
Figure 4:
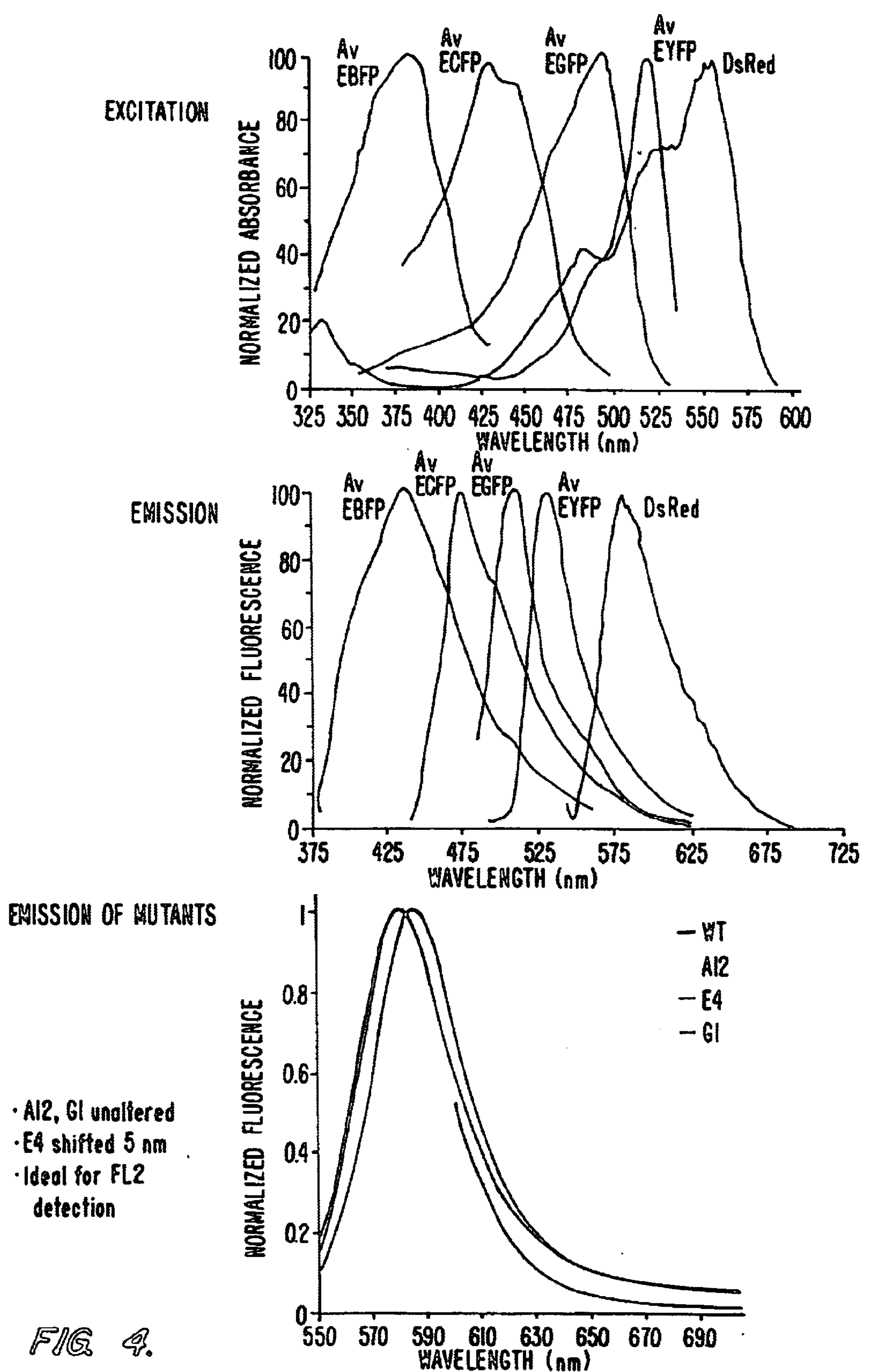
FIG. 4 shows excitation and emission spectra of certain mutants of the invention.

The present invention provides variants of Discosoma red fluorescent protein, which have enhanced brightness, expression, and/or folding kinetics. These improved characteristics are useful for functional screens as a reporter for gene transcription (e.g., as a fusion protein), for target characterization and localization of fusion proteins, and for scaffolds for protein and peptide libraries. For example, variants of the invention can be cloned into expression vectors that are used to express cDNA or random peptide libraries. The variant is positioned in the vector such that it forms a fusion protein with the expressed cDNA or peptide. The cDNA library can comprise sense, antisense, full length, and truncated cDNAs. The peptide library is encoded by nucleic acids. cDNA libraries are made from any suitable RNA source. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors. The Discosoma variant can thus be used as a selectable marker.

Red fluorescent protein is generally useful for screens employing FACS assays. Red fluorescent protein is also useful in screens for reporter gene transcription, fusion protein localization, yeast two hybrid experiments, immunoprecipitation and proteomics, increased affinity of receptors for fluorescently labeled ligands, proteins which increase the expression level of a second protein, altered immunogenicity for fluorescently labeled antibodies, changes in cell shape and size, changes in proton pump activity, relative DNA content in cell cycle and apoptosis, cellular localization and changes in metabolic rates of calcium flux, cell division, mitochondrial activity, pH, and free radical production. Such assays are useful for identifying proteins involved in the cell cycle, cellular proliferation, lymphocyteactivation, ubiquitination pathways, cancer, mast cell degranulation, viral replication and translation (e.g., HCV) and angiogenesis. In addition to red fluorescent protein, such screens can also use one or more additional fluorescent protein, such as *Aequorea Victoria* GFP, Zoanthus YFP and GFP, Aneomonia CFP, Clavularia CFP, *D. striata* CFP, *Renilla muelleri* GFP, *Renilla reniformis* GFP, and *Ptilosarcus gurneyi* GFP, and variants thereof.

In the present invention, novel methods of directed protein evolution were used to obtain improved variants of red fluorescent protein, as well as other proteins, including other fluorescent proteins as described above. In the methods of the invention, error prone PCR is used to randomly mutagenize a nucleic acid sequence encoding a protein of interest (see, e.g., Leung et al., *Techniques* 1:11–15 (1989); Calwell & Joyce, *PCR Methods and Applications,* 2:28–33 (1992); and Gramm et al., *Proc. Nat'l Acad. Sci. USA* 89:3576–3580 (1992)). The inherently low fidelity of Taq polymerase or other thermostable polymerases can be further decreased by the addition of Mn+, increasing the Mg2+ concentration, and using unequal dNTP concentrations. A preferred method of EP-PCR is described in Calwell & Joyce, *PCR Methods and Applications,* 2:28–33 (1992) and in *Current Protocols,* supra. Alternatively, other well know mutagenesis methods such as gene shuffling could be employed (see, e.g., U.S. Pat. No. 5,811,238, WO 99/41369, WO 99/41368, and WO 00/46344). The library of variant nucleic acids is then transferred to mammalian cells (e.g., Jurkat, A549, Phoenix A, or BJAB) using retroviral vectors. Variants are detected by any suitable assay, e.g., in the case a fluorescent protein, by FACS. Clones of interest are then rescued and isolated. As described in FIG. 1, this technique was used to identify four preferred sites of point mutations (amino acid substitutions) that lead to red fluorescent proteins with enhanced brightness, altered emission, higher expression, and/or enhanced folding kinetics (3° or 4° structure).

Definitions

The term "point mutation" refers to a deletion, addition, or substitution at a designed amino acid position in an amino acid or nucleotide sequence. Preferably, the term refers to an amino acid substitution.

"Discosoma red fluorescent protein" refers to a wild-type protein isolated from Discosoma species "red" (described and sequenced in Matz et al., *Nature Biotechnology* 17:969–973 (1999)), as well as a mammalian codon-optimized variant shown in FIG. 1.

"Nucleic acid" refers to deoxyribonucleotides or ribonucleotides and polymers thereof in single- or double-stranded form, or complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Nucleic acids also include complementary nucleic acids.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V);

6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "fluorescent" label may be detected by exciting the fluorochrome with the appropriate wavelength of light and detecting the resulting fluorescence. The fluorescence may be detected visually, or by the use of electronic detectors such as charge coupled devices (CCDs) or photomultipliers and the like. Similarly, enzymatic labels may be detected by providing the appropriate substrates for the enzyme and detecting the resulting reaction product. FACS analysis is a preferred method of detection when the label is in a cell.

EXAMPLES

The following example is provided by way of illustration only and not by way of limitation. Those of skill in the art will readily recognize a variety of noncritical parameters that could be changed or modified to yield essentially similar results.

Example 1

Error Prone PCR and Directed Evolution of Discosoma Red Species Fluorescent Proteins in Mammalian Cells To mutagenize Discosoma red fluorescent protein, a mammalian codon optimized variant (see FIG. 1) was cloned with a flag tag and mutagenized using error prone PCR according to methods known to those of skill in the art (see, e.g., *Current Protocols in Molecular Biology,* volume 1, unit 8.3 (Ausubel et al., eds, 1994); Saiki et al., *Science* 239:487 (1988); Leung et al., *Technique* 1:11–15 (1989); Caldwell & Joyce, *PCR Methods and Applications* 2:28–33 (1992); and Gramm et al., *Proc. Nat'l Acad. Sci. USA* 89:3576–3580 (1992)).

Figure 5:
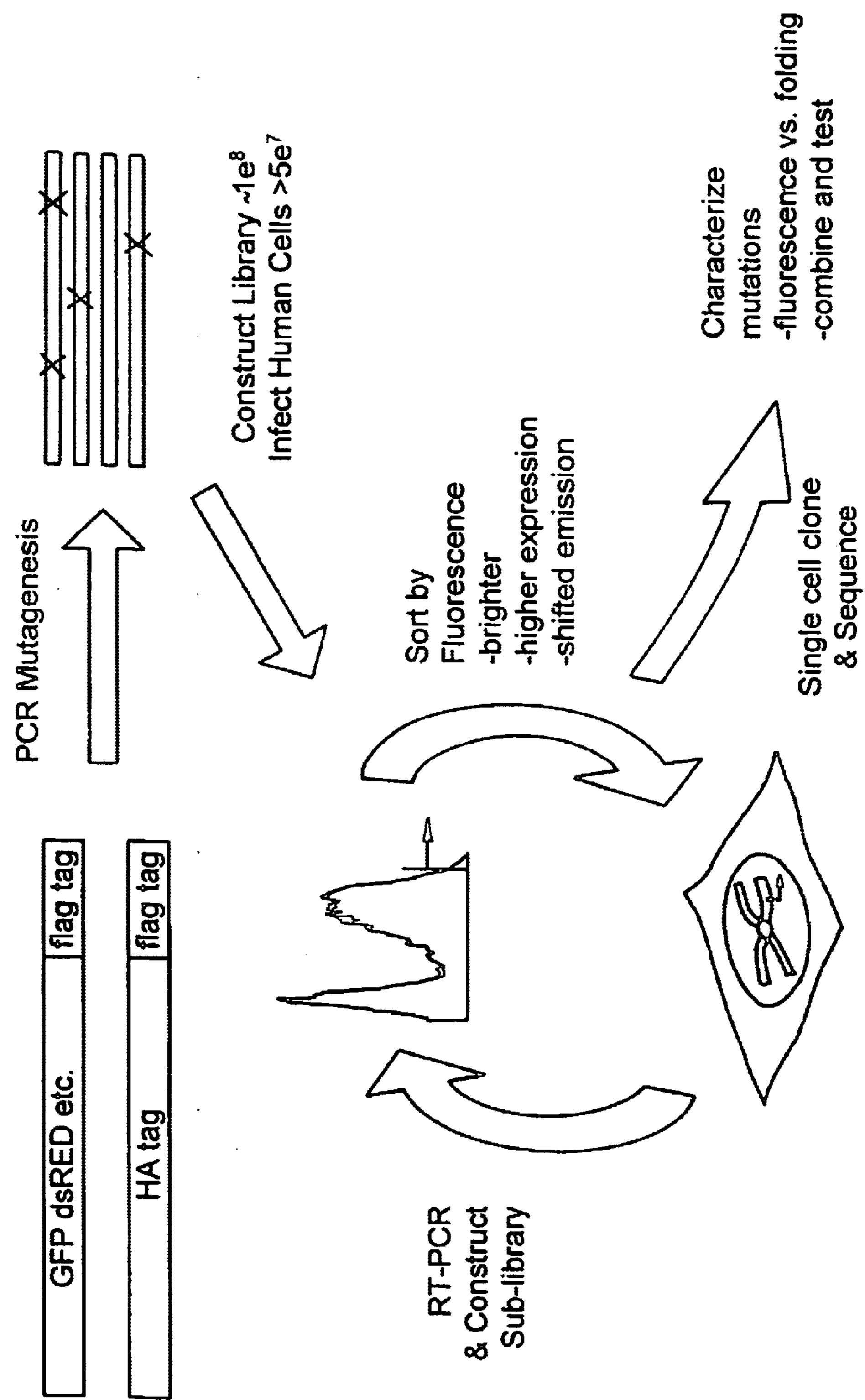
FIG. 5 shows a diagram of methods for directed evolution of proteins in mammalian cells.

The resulting library of mutagenized sequences was cloned into a retroviral vector expression library using RT-PCR and the retroviral library was used to infect human cells (BJAB cells). The cells were sorted for brighter fluorescence, higher expression, or shifted emission. Selected clones were isolated using RT-PCR, and sub-libraries were constructed and selected further with FACS (see FIG. 5). Single cell clones were isolated and sequenced.

FIG. 2 lists some of the brighter mutants identified in the screen (note: amino acid sequences are off by one from the sequence numbering described in FIG. 1 as the methionine was counted as zero for the purposes of the numbering in FIG. 2). FIG. 1 lists certain preferred mutations at amino acid positions N24, F125, K164 and M183, e.g., N24S/R/H; K125L/V; K164M; and M183K. These mutations can exist in the mutated variants alone or in any combination of one, two, three, or four, or optionally with additional point mutations at K93, R18, K139, E149, and D170, e.g., K93R, R18H, E149D, and D170G.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

---

What is claimed is:

1. An isolated nucleic acid comprising a nucleotide sequence encoding a Discosoma red fluorescent protein, wherein said Discosoma red fluorescent protein comprises an amino acid sequence as shown in FIG. 1 (SEQ ID NO:2) with one or more point mutations at an amino acid position selected from the group consisting of N24, F125, K164 and M183.

2. The nucleic acid of claim 1, wherein the nucleic acid is codon-optimized for expression in a mammalian cell.

3. A vector comprising the nucleic acid of claim 1.

4. The vector of claim 3, wherein the vector is a retroviral vector.

5. A host cell comprising the vector of claim 3.

6. The nucleic acid of claim 1, further comprising a nucleotide sequence encoding a second polypeptide.

7. The nucleic acid of claim 6, wherein said fluorescent protein and said second polypeptide are encoded in the form of a fusion protein.

8. The nucleic acid of claim 1, wherein said fluorescent protein comprises two, three, or four point mutations at an amino acid position selected from the group consisting of N24, F125, K164, and M183.

9. The nucleic acid of claim 1, wherein the point mutation at amino acid position N24 is a serine, arginine, or histidine substitution.

10. The nucleic acid of claim 1, wherein the point mutation at amino acid position F125 is a leucine or valine substitution.

11. The nucleic acid of claim 1, wherein the point mutation at amino acid position K164 is a methionine substitution.

12. The nucleic acid of claim 1, wherein the point mutation at amino acid position M183 is a lysine or threonine substitution.

13. The nucleic acid of claim 1, wherein said fluorescent protein comprises an amino acid sequence as shown in FIG. 1 (SEQ ID NO:2) with a leucine or valine substitution at amino acid position F125 and a lysine substitution at amino acid position M183.

14. The nucleic acid of claim 1, wherein said fluorescent protein comprises an amino acid sequence as shown in FIG. 1 (SEQ ID NO:2) with a leucine substitution at amino acid position F125 and a lysine substitution at amino acid position M183.

15. The nucleic acid of claim 1, wherein said fluorescent protein comprises an amino acid sequence as shown in FIG. 1 with a valine substitution at amino acid position F125 and a lysine substitution at amino acid position M183.

16. The nucleic acid of claim 1, wherein said fluorescent protein comprises an amino acid sequence as shown in FIG. 1 with a leucine or valine substitution at amino acid position F125 and a serine, arginine, or histidine substitution at amino acid position N24.

17. The nucleic acid of claim 1, wherein said fluorescent protein comprises an amino acid sequence as shown in FIG. 1 with a leucine substitution at amino acid position F125 and a serine substitution at amino acid position N24.

18. The nucleic acid of claim 1, wherein said fluorescent protein comprises an amino acid sequence as shown in FIG. 1 with a leucine or valine substitution at amino acid position F125, a serine, arginine, or histidine substitution at amino acid position N24, and a lysine substitution at amino acid position M183.

19. The nucleic acid of claim 1, wherein said fluorescent protein comprises an amino acid sequence as shown in FIG. 1 with a leucine substitution at amino acid position F125, a serine substitution at amino acid position N24, and a lysine substitution at amino acid position M183.

20. The nucleic acid of claim 1, wherein said fluorescent protein comprises an amino acid sequence as shown in FIG. 1 with a methionine substitution at amino acid position K164.

21. The nucleic acid of claim 1, wherein said fluorescent protein comprises an amino acid sequence as shown in FIG. 1 with a leucine substitution at amino acid position F125.

22. The nucleic acid of claim 1, further comprising one or more point mutations at an amino acid position selected from the group consisting of K93, R18, K139, E149, and D170.

23. The nucleic acid of claim 22, wherein the point mutation at amino acid position K93 is an arginine substitution.

24. The nucleic acid of claim 23, wherein the point mutation at amino acid position R18 is a histidine substitution.

25. The nucleic acid of claim 23, wherein the point mutation at amino acid position E149 is an aspartic acid substitution.

26. The nucleic acid of claim 23, wherein the point mutation at amino acid position D170 is a glycine substitution.

27. The nucleic acid of claim 25, wherein the protein comprises an amino acid sequence as shown in FIG. 1 with a leucine substitution at amino acid position F125, a serine substitution at amino acid position N24, a lysine substitution at amino acid position M183, and a histidine substitution at amino acid position R18.

28. The nucleic acid of claim 26, wherein the protein comprises an amino acid sequence as shown in FIG. 1 with a leucine substitution at amino acid position F125, a aspartic acid substitution at amino acid position E149, and a glycine substitution at amino acid position D170.

29. A method of making the fluorescent protein of claim 1, the method comprising the steps of:

(i) mutating a selected nucleotide sequence encoding a Discosoma red fluorescent protein comprising the amino acid sequence as shown in FIG. 1 (SEQ ID NO:2);

(ii) cloning the mutated sequence into an expression vector;

(iii) transfecting mammalian cells with the expression vector, and (iv) selecting said protein using FACS analysis.

30. The method of claim 29, wherein the selected nucleotide sequence is mutated using error prone PCR.

31. The method of claim 29, wherein the expression vector is a retroviral expression vector.

* * * * *